United States Patent [19]
Dominianni

[11] Patent Number: 4,629,811
[45] Date of Patent: Dec. 16, 1986

[54] 3-SULFONYLAMINO-4-AMINOBENZOPHE-
NONE DERIVATIVES

[75] Inventor: Samuel J. Dominianni, Indianapolis, Ind.

[73] Assignee: Eli Lilly and Company, Indianapolis, Ind.

[21] Appl. No.: 644,588

[22] Filed: Aug. 27, 1984

Related U.S. Application Data

[62] Division of Ser. No. 373,945, May 3, 1982, Pat. No. 4,483,986.

[51] Int. Cl.$^4$ .................. C07C 143/74; C07C 143/77
[52] U.S. Cl. ......................................... 564/99; 564/80
[58] Field of Search .................................. 564/80, 99

[56] References Cited

U.S. PATENT DOCUMENTS

| 4,118,742 | 10/1978 | Paget et al. | 548/306 |
| 4,174,454 | 11/1979 | Paget et al. | 548/306 |
| 4,313,000 | 1/1982 | Kruse et al. | 564/99 |
| 4,501,921 | 2/1985 | Ryan et al. | 564/99 |

FOREIGN PATENT DOCUMENTS 885843 12/1961 United Kingdom .

Primary Examiner—Robert W. Ramsuer
Attorney, Agent, or Firm—Charles W. Ashbrook

[57] ABSTRACT

A process is provided which produces 3-sulfonylamino-4-aminobenzophenone intermediates useful in the regiospecific synthesis of benzimidazole antiviral agents.

4 Claims, No Drawings

3-SULFONYLAMINO-4-AMINOBENZOPHENONE DERIVATIVES

This application is a division of application Ser. No. 373,945, filed May 3, 1982, now U.S. Pat. No. 4,483,986.

BACKGROUND OF THE INVENTION

Certain 1-sulfonylbenzimidazole compounds have been found to be useful as inhibitors of viral growth (U.S. Pat. Nos. 4,118,742 and 4,174,454). Of this series, 2-amino-5(6)benzoyl-1-sulfonylbenzimidazoles were found to be potent antiviral agents and also to be useful as intermediates in preparing similarly active derivatives.

In the above terminology, it is recognized that an isomeric mixture of 5- and 6-benzoyl benzimidazoles is obtained when a sulfonyl chloride is allowed to react with a "tautomeric benzimidazole", i.e., a benzimidazole reactant which can be substituted at either nitrogen atom. Such an isomeric mixture of compounds is indicated by numbering the alternate positions as 5(6). Upon sulfonylation, the isomeric mixture can be resolved into the two individual compounds by means of fractional crystallization and/or by column chromatography.

Although both isomers of any given substitution were found to inhibit polio virus growth, it was recognized that the 6-isomer is generally more potent than the corresponding 5-isomer. Since the 6-isomers are preferred, and in that the separation techniques described above are expensive, time-consuming, and low yielding due to handling and the loss of half the mixture as the less desired 5-isomer, a more efficient, specific synthesis of the 6-isomer is desirable.

In supplying such a regioselective synthesis, this invention provides previously unknown compounds which are useful as intermediates in preparing 6-benzoyl-2-amino-1-sulfonylbenzimidazoles and a novel method for their preparation. Some of the novel intermediates claimed in this invention have been prepared by an alternate process as disclosed by C. W. Ryan's application filed at even date herewith entitled "Selective Sulfonation Process", Ser. No. 373,944.

SUMMARY OF THE INVENTION

This invention provides a process for the preparation of novel compounds represented by the formula

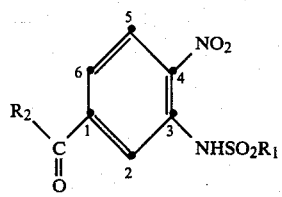

wherein, $R_1$ is $C_1$–$C_5$ alkyl, $C_3$–$C_7$ cycloalkyl, phenyl, furyl, thienyl, thiazol-2-yl, 1,3,4-thiadiazol-2-yl, 2-methyl-1,3,4-thiadiazol-5-yl, or $R_4R_5N$-, wherein $R_4$ and $R_5$ are independently $C_1$–$C_3$ alkyl or $R_4$ and $R_5$ when taken together with the nitrogen atom to which they are attached, are pyrrolidino, piperidino or morpholino; and $R_2$ is phenyl or phenyl substituted by $C_1$–$C_4$ alkyl, $C_1$–$C_4$ alkoxy, chloro, bromo, iodo, or trifluoromethyl.

These compounds and the corresponding 4-amino analogs of the formula II derived therefrom

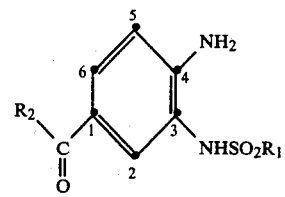

wherein $R_1$ and $R_2$ are the same as described hereinabove, are useful intermediates in the preparation of 6-benzoyl-2-amino-1-sulfonylbenzimidazole antiviral agents.

The compounds of this invention are prepared by reacting a fluoronitrobenzene compound of the formula

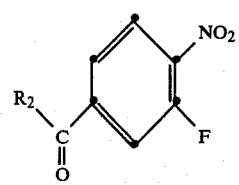

with the anion of a sulfonamide having the formula

$$R_1SO_2NH_2 \qquad IV$$

wherein $R_1$ and $R_2$ are as defined hereinabove. The resulting nitrobenzophenones (I), are transformed to their respective aniline derivatives (II) which are in turn converted into the desired benzimidazoles.

DETAILED DESCRIPTION AND PREFERRED EMBODIMENT

A preferred group of compounds prepared by this process are those compounds wherein $R_2$ is unsubstituted phenyl.

Another preferred group of compounds prepared by this process are those compounds wherein $R_1$ is $C_1$–$C_5$ alkyl, especially isopropyl.

Two especially preferred compounds of this invention are 3-(isopropylsulfonyl)amino-4-nitrobenzophenone and 3-(isopropylsulfonyl)amino-4-aminobenzophenone.

The following definitions refer to the various terms used throughout this disclosure. The term "furyl" refers to the furan radical attached at the 2 or 3 position. The term "thienyl" refers to the thiophene radical attached at the 2 or 3 position. The term "thiazol-2-yl" or "2-thiazole" refers to the thiazole radical attached at the 2-position. The term "1,3,4-thiadiazol-2-yl" or "thiadiazol-2-yl" refers to the 1,3,4-thiadiazole radical attached at the 2-position. The term "2-methyl-1,3,4-thiadiazol-5-yl" refers to a 2-methyl-1,3,4-thiadiazole radical attached at the 5-position.

The term "$C_1$–$C_5$ alkyl" refers to the straight and branched aliphatic radicals of one to five carbon atoms such as methyl, ethyl, propyl, isopropyl, butyl, isobutyl, sec-butyl, tert-butyl, amyl, isoamyl, secamyl, sec-isoamyl (1,2-dimethylpropyl), and tert-amyl (1,1-dimethylpropyl). The term $C_1$–$C_5$ alkyl includes within its definition the terms "$C_1$–$C_3$ alkyl" and "$C_1$–$C_4$ alkyl".

The term "C_3-C_7 cycloalkyl" refers to the saturated alicyclic rings of three to seven carbon atoms such as cyclopropyl, methylcyclopropyl, cyclobutyl, cyclopentyl, cyclohexyl, 1-, 2-, 3- or 4-methylcyclohexyl and cycloheptyl.

The term "$C_1-C_4$ alkoxy" includes the straight and branched aliphatic ether radicals of one to four carbon atoms such as methoxy, ethoxy, propoxy, isopropoxy, butoxy, isobutoxy, sec-butoxy, and tertbutoxy.

The reaction is generally carried out by the addition of the 3-fluoro-4-nitrobenzophenone of formula III to a solution of the previously prepared anion of the sulfonamide. This anion is formed in situ by the action of a strong base on the sulfonamide in a compatible solvent. As those skilled in the art will recognize, the base employed must be strong enough to generate the anion of the particular sulfonamide. While sodium hydride is generally preferred, other bases include alkali metal amides and hydrides such as sodium or potassium amide, potassium hydride, and lithium amide, potassium t-butoxide, and the like. Suitable non-reactive solvents include dimethylsulfoxide, N,N-dimethylformamide, ethers such as diethylether, tetrahydrofuran, and dimethoxyethane, aromatic hydrocarbons such as benzene, toluene, and xylene, and the like. The formation of the sulfonamide anion is generally carried out by adding the sulfonamide to a solution or suspension of the base in the solvent with the exclusion of moisture at a temperature of 0°-100° C., preferably at 0°-30° C.

After the 3-fluoro-4-nitrobenzophenone is added to a solution of the anion, the reaction is allowed to proceed at a temperature of 0°-100° C., preferably at ambient temperature, until complete, usually about 1 to 6 hours. Preferred workup of the reaction includes quenching and neutralization of the mixture with acidic ice water, extraction of the product into an organic solvent such as ethyl acetate, ether, or dichloromethane, and evaporation of the solvent to provide the crude product. The crude product may be used without purification for the subsequent reduction and cyclization to the desired benzimidazole, or first purified by conventional techniques such as crystallization and/or chromatography.

The 3-fluoro-4-nitrobenzophenone compounds (III) which are required in the foregoing process are readily prepared by the Friedel-Crafts acylation of a 3-fluoro-4-nitrobenzoyl halide, preferably the acid chloride, on the appropriately substituted benzene derivative $R_2H$. The classical conditions for such a reaction can be employed; a slight molar excess of a Lewis acid, such as aluminum chloride, hydrogen fluoride, sulfuric acid, aluminum bromide, ferric chloride, and the like, is used, the preferred catalyst being aluminum chloride. The solvent that is used is preferably the same solvent that was used in preparing the acid chloride from the corresponding benzoic acid. In the present invention, an excess of the $R_2H$ reactant can be employed as both the solvent of acylation and of acid chloride formation, although the use of a cosolvent, such as N,N-dimethylformamide may be used.

It is recognized that in performing a Friedel-Crafts acylation upon a substituted benzene ($R_2H$), more than one positional isomer may be obtained. Those skilled in the art will also recognize that such isomeric mixtures may be resolved into the individual compounds as the nitrobenzophenones, or after the nitrobenzophenone mixture has been transformed by one or more of the subsequent steps which ultimately produce the desired benzimidazoles. The isomers are most conveniently resolved through fractional crystallization and/or chromatography. In the preferred case of $R_2$ being unsubstituted phenyl, no isomer problem exists. For the incorporation of those substituents of the $R_2$ ring which deactivate the ring and are not suitable substrates for acylation, functionalization may be performed after the acylation step; for example, upon the 6-benzoylbenzimidazole or the intermediate benzophenone. Reactions such as nitrations, reductions, oxidations, sulfonylations, halogenations, and similar transformations may be performed to introduce the desired substituents into either an unsubstituted or previously substituted $R_2$ ring.

The intermediate 3-fluoro-4-nitrobenzoyl halide is prepared from 3-fluoro-4-nitrobenzoic acid by the action of a suitable inorganic acid halide. In the preferred case of the acid chloride intermediate, the use of thionyl chloride is particularly convenient in this conversion because the by-products are gaseous and the excess reagent can be removed by distillation. Other suitable reagents include phosphorous pentachloride, phosphorous trichloride, and phosphoryl chloride. This conversion can be performed in a non-reactive solvent with isolation of the acyl chloride, or preferably in situ using $R_2H$ as both the solvent and subsequent reactant/solvent in the following acylation step.

The intermediate 3-fluoro-4-nitrobenzoic acid can be prepared by the permanganate oxidation of commercially available 3-fluoro-4-nitrotoluene according to the procedure of Schmeles and Rubin, *J. Am. Chem. Soc.*, 66, 1632 (1944).

The sulfonamide compounds (IV) required as starting materials in the foregoing process can be readily prepared by the treatment of the respective sulfonyl chlorides with ammonia as summarized by J. March in *Advanced Organic Chemistry: Reactants, Mechanisms, and Structure*, McGraw-Hill, Inc., New York, 1968, p. 374.

Among the sulfonyl chloride compounds which are required as reactants, methanesulfonyl chloride (mesyl chloride), isopropylsulfonyl chloride, dimethylsulfamoylchloride, benzenesulfonyl chloride and 2-thiophenesulfonyl chloride are commercially available. The preparation of 3-thiophenesulfonyl chloride and 2(or 3)-furansulfonyl chloride is described by Arcoria et al., *J. Org. Chem.*, 39, 1689 and 3595 (1974). 2-Thiazolesulfonyl chloride, 2-thiadiazolesulfonyl chloride, and 2-methyl-5-thiadiazolesulfonyl chloride are available from 2-thiazolethiol, 2-thiadiazolethiol and 2-methyl-5-thiadiazolethiol, respectively, by oxidation of the thiol function with chlorine in aqueous solution. Other $C_1-C_5$ alkyl and $C_3-C_7$ cycloalkyl sulfonyl chlorides can be prepared by the chlorination of the appropriate alkyl thiol or by reacting sulfuryl chloride with sodium alkyl sulfonates derived from the corresponding carbinols and sulfuric acid. The N,N-dialkylsulfamoyl chlorides can be prepared as described by Bindely et al., *J. Am. Chem. Soc.*, 61, 3250 (1939), by reacting a secondary amine salt with sulfuryl chloride. Alternatively, they can be prepared by reacting a chloramine compound of the formula

$$R_4R_5N-Cl$$

with sulfur dioxide at a temperature of −5° to 30° C. The chloramine compounds are prepared by reacting the corresponding secondary amines with antimony pentachloride, sodium hypochlorite or sulfuryl chloride.

Further illustrative of the sulfonyl chlorides which can be reacted with the benzophenone compounds are ethyl-, propyl-, isopropyl-, butyl-, isobutyl-, sec-butyl-, tert-butyl-, amyl-, isoamyl-, sec-isoamyl-, and tert-amylsulfonyl chloride in addition to cyclobutyl-, cyclopentyl-, cyclohexyl-, and cycloheptylsulfonylchloride.

Other sulfamoyl chlorides which can be employed are diethyl-, dipropyl-, N-methyl-N-ethyl-, N-methyl-N-propyl-, N-ethyl-N-propyl-, N-methyl-N-isopropyl-, N-ethyl-N-isopropyl-, N-propyl-N-isopropyl-, diisopropyl-, pyrrolidino-, piperidino-, and morpholinosulfamoylchloride.

The 3-sulfonylamino-4-nitrobenzophenone compounds of this invention can be transformed into the antiviral benzimidazoles mentioned previously through the following procedures.

The 3-sulfonylamino-4-nitrobenzophenone intermediates (I) can be transformed into the corresponding 3-sulfonylamino-4-aminobenzophenone compounds (II), by chemical reduction or catalytic hydrogenation. Suitable methods of chemical reduction include aqueous treatment with sodium hydrosulfite, treatment with zinc, tin, or iron in the presence of a mineral acid, or the like. Catalytic hydrogenation may be performed in a non-reactive solvent, such as ethanol or tetrahydrofuran, employing a suitable catalyst such as Raney nickel, platinum oxide, palladium-on-carbon, and the like.

The 3-sulfonylamino-4-aminobenzophenone thus formed may be cyclized to the respective 2-aminobenzimidazole by the reaction with cyanogen bromide or cyanamide in a suitable solvent, such as an alcohol, in the presence of a base which is of sufficient basicity so as to generate the sulfonamide anion, such as sodium hydroxide or sodium carbonate. The 6-benzoyl-2-amino-1-sulfonylbenzimidazoles prepared in this manner are identical to the 6-benzoyl isomers described as antiviral agents in U.S. Pat. No. 4,118,742.

Illustrative of the compounds that can be prepared by this process are the following:
3-(methylsulfonyl)amino-4-nitrobenzophenone,
3-(dipropylaminosulfonyl)amino-4-nitro-4'-chlorobenzophenone,
3-(2-furylsulfonyl)amino-4-nitro-4'-methoxybenzophenone,
3-(1,3,4-thiadiazol-2-ylsulfonyl)amino-4-nitro-2'-methylbenzophenone,
3-(N-ethyl-N-methylaminosulfonyl)amino-4-nitrobenzophenone,
3-(cyclopropylsulfonyl)amino-4-nitro-4'-n-butylbenzophenone,
3-(benzenesulfonyl)amino-4-nitro-4'-trifluoromethylbenzophenone,
3-(morpholinosulfonyl)amino-4-nitro-2'-chlorobenzophenone,
3-(dimethylaminosulfonyl)amino-4-nitro-3'-propoxybenzophenone,
3-(pyrrolidinosulfonyl)amino-4-nitro-4'-bromobenzophenone,
3-(3-thienylsulfonyl)amino-4-nitro-2'-ethylbenzophenone,
3-(cyclohexylsulfonyl)amino-4-nitro-4'-ethoxybenzophenone,
3-(2-methyl-1,3,4-thiadiazol-5-ylsulfonyl)amino-4-nitro-2'-methylbenzophenone,
3-(cyclopentylsulfonyl)amino-4-nitro-3'-propylbenzophenone,
3-(2-thienylsulfonyl)amino-4-nitro-4'-propoxybenzophenone,
3-(dipropylaminosulfonyl)amino-4-nitro-3'-trifluoromethylbenzophenone,
3-(t-butylsulfonyl)amino-4-nitro-2'-bromobenzophenone,
3-(cycloheptylsulfonyl)amino-4-nitro-3',4'-dichlorobenzophenone,
3-(piperidinosulfonyl)amino-4-nitro-4'-methoxybenzophenone,
3-(isopropylsulfonyl)amino-4-nitro-3',4'-dimethoxybenzophenone,
3-(diethylaminosulfonyl)amino-4-nitro-4'-methoxy-3'-bromobenzophenone,
3-(n-pentylsulfonyl)amino-4-nitro-4'-butoxybenzophenone,
3-(dimethylaminosulfonyl)amino-4-nitro-4'-chlorobenzophenone,
3-(N-methyl-N-propylaminosulfonyl)amino-4-nitro-3'-bromo-4'-chlorobenzophenone,
3-(ethylsulfonyl)amino-4-nitro-4'-trifluoromethylbenzophenone,
3-(diethylaminosulfonyl)amino-4-nitrobenzophenone,
3-(3-furylsulfonyl)amino-4-nitro-3',4'-dibromobenzophenone,
3-(cyclopropylsulfonyl)amino-4-nitro-3'-ethoxy-4'-methoxybenzophenone,
3-(1,3,4-thiadiazol-2-ylsulfonyl)amino-4-nitro-2'-trifluoromethylbenzophenone,
3-(morpholinosulfonyl)amino-4-nitro-2'-methyl-4'-methoxybenzophenone,
3-(t-butylsulfonyl)amino-4-nitro-3'-propyl-4'-methylbenzophenone,
3-(phenylsulfonyl)amino-4-nitrobenzophenone,
3-(methylsulfonyl)amino-4-nitro-3',4'-dimethylbenzophenone,
3-(dimethylaminosulfonyl)amino-4-nitro-3'-methoxy-4'-chlorobenzophenone,
3-(2-furylsulfonyl)amino-4-nitro-2'-methylbenzophenone,
3-(2-methyl-1,3,4-thiadiazol-5-ylsulfonyl)amino-4-nitro-3',4'-dichlorobenzophenone,
3-(piperidinosulfonyl)amino-4-nitro-4'-isopropoxybenzophenone,
3-(cyclobutylsulfonyl)amino-4-nitro-3'-sec-butylbenzophenone,
3-(N-methyl-N-ethylaminosulfonyl)amino-4-nitro-3'-methylbenzophenone,
3-(4-methylcyclohexylsulfonyl)amino-4-nitro-4'-trifluoromethylbenzophenone,
3-(pyrrolidinosulfonyl)amino-4-nitro-2'-bromobenzophenone,
3-(1,2-dimethylpropylsulfonyl)amino-4-nitro-3',4'-dimethoxybenzophenone,
3-(2-methylcyclohexylsulfonyl)amino-4-nitro-4'-iodobenzophenone,
3-(methylcyclopropylsulfonyl)amino-4-nitro-4'-t-butoxybenzophenone,
3-(cyclohexylsulfonyl)amino-4-nitrobenzophenone, and
3-(thiazol-2-ylsulfonyl)amino-4-nitro-2'-methoxybenzophenone.

The following examples further illustrate the preparation of the starting materials, intermediates, and compounds of this invention as well as their conversion to the desired 6-benzoyl-2-amino-1-sulfonylbenzimidazole antiviral compounds.

Preparation 1

3-Fluoro-4-nitrobenzoic acid

The title compound was prepared in a 39% yield by the permanganate oxidation of 3-fluoro-4-nitrotoluene as described by Schmeles and Rubin, *J. Am. Chem Soc.*, 66, 1632 (1944).

Preparation 2

3-Fluoro-4-nitrobenzophenone

A solution of 14.61 g. (0.079 m.) of 3-fluoro-4-nitrobenzoic acid, 200 ml. of benzene, 10 ml. of thionyl chloride, and 1 ml. of N,N-dimethylformamide was stirred overnight at room temperature under a calcium chloride drying tube. The resulting clear solution was then heated to reflux for one hour, after which time the solution was concentrated to approximately 75% of the original volume by distillation. The mixture was cooled by placing the flask in an ice bath. With additional cooling, 20 g. of aluminum chloride was added in portions through Gooch tubing over a period of about 45 minutes. The resulting dark mixture was stirred and allowed to warm to room temperature overnight. The reaction flask was again cooled in an ice bath as 300 ml. of 1N hydrochloric acid was added dropwise. The mixture was extracted several times with ethyl acetate and the combined extracts were washed with water, a saturated solution of sodium bicarbonate, water, a saturated solution of sodium chloride, and then dried over magnesium sulfate. Filtration and evaporation of the solvent in vacuo provided 16.8 g. (87% yield) of the desired compound as an oil which solidified on scratching. Recrystallization from 95% ethanol afforded yellow needles, m.p. about 77°–79° C.

Analysis: $C_{13}H_8FNO_3$: Calculated: C, 63.68; H, 3.29; N, 5.71; F, 7.75; Found: C, 63.57; H, 3.02; N, 5.66; F, 7.70.

EXAMPLE 1

3-(Isopropylsulfonyl)amino-4-nitrobenzophenone

To 50 ml. of dimethylsulfoxide (DMSO) was added 1.01 g. (0.021 m.) of 50% sodium hydride in oil. After the initial gas evolution ceased, 2.53 g. (0.0206 m.) of isopropylsulfonamide [prepared according to Duguet, *Rec. Trav. Chim.*, 25, 215 (1906)] was added. The mixture was stirred under a calcium chloride drying tube for ten minutes after which time 4.90 g. (0.020 m.) of 3-fluoro-4-nitrobenzophenone was added, followed by 20 ml. of DMSO. After stirring for five hours at room temperature, the reaction solution was poured into a mixture of ice and 1N hydrochloric acid which was then extracted several times with ethyl acetate. The extracts were combined, washed with water, and dried over magnesium sulfate. The oil remaining after evaporation was triturated with isopropanol to give 6.65 g. (95% yield) of 3-(isopropylsulfonyl)amino-4-nitrobenzophenone as a yellow powder. Crystallization from isopropanol gave pale yellow needles, m.p. about 115°–116° C.

Analysis: $C_{16}H_{16}N_2O_5S$: Calculated: C, 55.16; H, 4.63; N, 8.04; S, 9.20; Found: C, 55.06; H, 4.65; N, 7.93; S, 9.16.

EXAMPLE 2

3-(Isopropylsulfonyl)amino-4-aminobenzophenone

A solution of 3.91 g. (0.0112 m.) of 3-(isopropylsulfonyl)amino-4-nitrobenzophenone in 60 ml. of tetrahydrofuran (THF) was added dropwise over a period of 30 minutes to a stirred solution of 23.7 g. of sodium hydrosulfite in 200 ml. of water. After 60 minutes of additional stirring, solid sodium chloride was added and the layers were separated. The aqueous layer was extracted with THF, and the combined THF extracts were washed with a saturated solution of sodium chloride. Evaporation of the THF gave crude 3-(isopropylsulfonyl)amino-4-aminobenzophenone which was used without further purification in the subsequent cyclization. A small sample was crystallized from isopropanol several times to give the pure compound as colorless blocks, m.p. about 143°–145° C.

Analysis: $C_{16}H_{18}N_2O_3S$: Calculated: C, 60.36; H, 5.70; N, 8.80; S, 10.07; Found: C, 60.46; H, 5.75; N, 8.59; S, 10.30.

EXAMPLE 3

6-Benzoyl-2-amino-1-isopropylsulfonylbenzimidazole

A solution of 3-(isopropylsulfonyl)amino-4-aminobenzophenone from Example 2 in approximately 50 ml. of isopropanol was treated with 1.2 g. of cyanogen bromide and 5 ml. of 2N sodium hydroxide. After stirring at room temperature for two hours, an additional 1.6 g. of cyanogen bromide was added. The reaction was stirred overnight and then treated with a saturated solution of ammonium chloride. The solution was extracted several times with ethyl acetate. The combined extracts were washed with water and then a solution of saturated sodium chloride, dried over sodium sulfate, and evaporated. Trituration with fresh ethyl acetate gave 1.71 g. [50% yield from the 3-(isopropylsulfonyl)amino-4-nitrobenzophenone of Example 2]of 6-benzoyl-2-amino-1-isopropylsulfonylbenzimidazole as a brown powder. Charcoal treatment and recrystallization from THF-ethyl acetate gave off-white granules, m.p. about 191°–193° C.

Analysis: $C_{17}H_{17}N_3O_3S$: Calculated: C, 59.46; H, 4.99; N, 12.24; S, 9.34; Found: C, 59.20; H, 4.72; N, 12.14; S, 9.39.

I claim:

1. A compound of the formula II

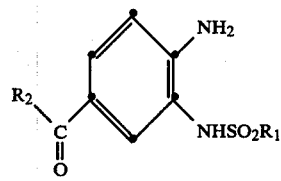

wherein
 $R_1$ is $C_1$–$C_5$ alkyl or $C_{3-7}$ cycloalkyl and
 $R_2$ is phenyl or phenyl substituted by $C_1$–$C_4$ alkyl, $C_1$–$C_4$ alkoxy, chloro, bromo, iodo, or trifluoromethyl.

2. A compound of claim 1 wherein $R_2$ is phenyl.
3. A compound of claim 1 wherein $R_1$ is isopropyl.
4. The compound of claim 1 which compound is 3-(isopropylsulfonyl)amino-4-aminobenzophenone.

* * * * *